(12) United States Patent
Popovic et al.

(10) Patent No.: US 8,089,417 B2
(45) Date of Patent: Jan. 3, 2012

(54) MICROWAVE SCANNING SYSTEM AND MINIATURIZED MICROWAVE ANTENNA

(75) Inventors: Milica Popovic, Montreal (CA); Houssam Kanj, Waterloo (CA)

(73) Assignee: The Royal Institution for the Advancement of Learning/McGill University, Montreal (CA)

( * ) Notice: Subject to any disclaimer, the term of this patent is extended or adjusted under 35 U.S.C. 154(b) by 691 days.

(21) Appl. No.: 12/130,731

(22) Filed: May 30, 2008

(65) Prior Publication Data

US 2009/0015832 A1    Jan. 15, 2009

Related U.S. Application Data

(60) Provisional application No. 60/941,294, filed on Jun. 1, 2007.

(51) Int. Cl.
*H01Q 21/20* (2006.01)
(52) U.S. Cl. .................................. 343/795; 343/700 MS
(58) Field of Classification Search .................. 343/795, 343/797, 700 MS, 821
See application file for complete search history.

(56) References Cited

U.S. PATENT DOCUMENTS

| | | | |
|---|---|---|---|
| 5,428,364 A * | 6/1995 | Lee et al. ....................... | 343/767 |
| 6,046,704 A * | 4/2000 | Lopez ............................ | 343/821 |
| 6,061,589 A | 5/2000 | Bridges et al. | |
| 7,209,089 B2 * | 4/2007 | Schantz ........................ | 343/787 |
| 7,372,417 B2 * | 5/2008 | Fukuchi ........................ | 343/767 |
| 2003/0088180 A1 | 5/2003 | Van Veen et al. | |
| 2005/0107693 A1 | 5/2005 | Fear et al. | |
| 2008/0180342 A1* | 7/2008 | Kerselaers .................... | 343/795 |

* cited by examiner

*Primary Examiner* — Tan Ho
(74) *Attorney, Agent, or Firm* — Goudreau Gage Dubuc; Hugh Mansfield

(57) ABSTRACT

A micro strip antenna comprising a planar substrate fabricated from a dielectric material and a pair of like elements arranged in mirror image on the planar substrate, each of the elements comprising a radiating portion comprising an elongate conductive strip of a constant thickness, the elongate conductive strip comprising first arcuate side edges mutually diverging between a narrow end and a wide end. There is also disclosed a system for detecting the presence of a region having a first dielectric constant within a medium having a second dielectric constant different from the first dielectric constant, such as a tumour embedded in a fatty tissue. The system comprises a support fabricated from a material having a dielectric constant substantially the same as the second dielectric constant, a scanner array comprising a plurality of scanning elements embedded in the support, each of the scanning elements directing a series of microwave pulses into the medium and receiving backscatter returns resulting from the series of microwave pulses, and an analyzer coupled to each of the scanning elements, the analyzer collecting the backscatter returns and processing the backscatter returns to detect the region.

10 Claims, 17 Drawing Sheets

MICROWAVE SCANNING SYSTEM AND MINIATURIZED MICROWAVE ANTENNA

CROSS REFERENCE TO RELATED APPLICATIONS

The present application claims priority on U.S. Provisional Application Ser. No. 60/941,294 filed on Jun. 1, 2007 which is incorporated herein in its entirety by reference.

FIELD OF THE INVENTION

The present invention relates to a microwave scanning system and miniaturized microwave antenna. In particular, the present invention relates to a system implementing the miniaturized antenna for emitting microwaves and detecting backscatter which is subsequently analysed for detecting anomalies embedded in bodies.

BACKGROUND OF THE INVENTION

Microwave imaging systems are currently used in a variety of applications for detecting the presence and location of buried objects based on the reflections of microwave radiation. These systems typically illuminate a composite having specific dielectric properties with electromagnetic (EM) waves, which penetrate into the material where they interact with its interior. The waves are then reflected back from the material's subsurface defects and their properties are monitored to convey information about the composite at hand. Since most dielectric materials such as clothing, paper, and plastic are nearly transparent over the spectral band of microwave radiation, microwave imaging shows promising results in a variety of applications ranging from security inspection systems to ground penetrating radars. Moreover, as it is non-ionizing at moderate power levels, microwave radiation has the advantage over a number of other sources of radiation of posing no known health risk. As a result, microwaves appear well suited to biological sensing applications. More specifically, microwave imaging overcomes several limitations of common early-stage breast cancer detection systems such as mammography, ultrasound and Magnetic Resonance Imaging (MRI). X ray mammography, for example, exposes patients to low levels of ionizing radiation and often results in false diagnostic. It is also uncomfortable as breast compression is often required to reduce image blurring and to create tissue uniformity.

At microwave frequencies a significant dielectric contrast between normal and malignant tissue is found. Typical ex-vivo breast tissue, for instance, has a relative dielectric constant of about 10, while a malignant tumour has a relative dielectric constant in the range of 45-55. As a result, less attenuation and reflection are expected from normal than from malignant tissues and the tumour microwave scattering cross-section is much larger than that of a normal breast tissue with the same size. Moreover, healthy, fatty tissues are relatively translucent to microwaves since attenuation in normal breast tissue is low enough to make signal propagation through even large breast volumes quite feasible. Microwave imaging is therefore a safe, comfortable, sensitive and accurate method, which is attractive for early breast cancer detection. Existing approaches use antennas to illuminate the breast area with an ultra-wide band pulse and detect the energy reflected from or transmitted through the breast, from which images are formed to indicate the locations of strongly scattering objects. Additionally, several antennas are typically arranged to form an array, which enables scanning of a number of locations surrounding the breast.

A plurality of antenna designs has been disclosed in the art for microwave imaging applications. However, these antennas have various drawbacks such as their large size and non-planar structure, which make them difficult to use as a base for an antenna array of several elements. Bowtie antennas, for example, are often favoured for their remarkable broadband properties. The main concern however is the reflection from the antenna ends, which can be minimized with variable resistive loading. However, parameters required for the suggested design, such as a specific variation of the resistive loading and the equivalent surface resistance of the antenna, challenge its practical implementation. In addition, the antenna's overall efficiency could be significantly lowered by the high value of the equivalent surface resistance.

What is therefore needed, and an object of the present invention, is a planar and ultra-compact antenna for use in microwave imaging systems, where the antenna has constant resistive loading and reflection from the antenna ends is minimized through a change in the antenna geometry.

SUMMARY OF THE INVENTION

In order to address the above and other drawbacks, there is disclosed a micro strip antenna for terminating a transmission line comprising a pair of conductors. The antenna comprises a planar substrate fabricated from a dielectric material and a pair of like elements arranged in mirror image on the planar substrate, each of the elements comprising a radiating portion comprising an elongate conductive strip of a first constant thickness, the elongate conductive strip comprising first arcuate side edges mutually diverging between a narrow end and a wide end. Each of the elongate conductive strips is interconnected at the narrow end to a respective one of the pair of conductors.

In a particular embodiment, each of the like elements further comprises a dissipating portion on the planar substrate, the dissipating portion comprising an elongate resistive strip interconnected to the conductive strip along an edge at the wide end, the elongate resistive strip of a second constant thickness and comprising second arcuate side edges mutually converging between the wide end and a tip and wherein each of the second arcuate side edges is a differentiable continuation of a respective one of the first arcuate side edges.

There is also disclosed a system for detecting the presence of a region having a first dielectric constant within a medium having a second dielectric constant different from the first dielectric constant. The system comprises a support fabricated from a material having a dielectric constant substantially the same as the second dielectric constant, a scanner array comprising a plurality of scanning elements embedded in the support, each of the scanning elements directing a series of microwave pulses into the medium and receiving backscatter returns resulting from the series of microwave pulses, and an analyzer coupled to each of the scanning elements, the analyzer collecting the backscatter returns and processing the backscatter returns to detect the region.

Furthermore, there is disclosed a scanning element for use in a microwave scanning system. The scanning element comprises a pair of like substantially flat wideband antennas, each of the antennas comprising a planar substrate fabricated from a dielectric material, a pair of radiating elements arranged on a surface of the substrate in a bowtie configuration and a balun. A first of the wideband antennas is positioned at right angles to a second of the wideband antennas.

Other objects, advantages and features of the present invention will become more apparent upon reading of the following non-restrictive description of specific embodiments thereof, given by way of example only with reference to the accompanying drawings.

DETAILED DESCRIPTION OF THE ILLUSTRATIVE EMBODIMENTS

The present invention is illustrated in further details by the following non-limiting examples.

Figure 1:
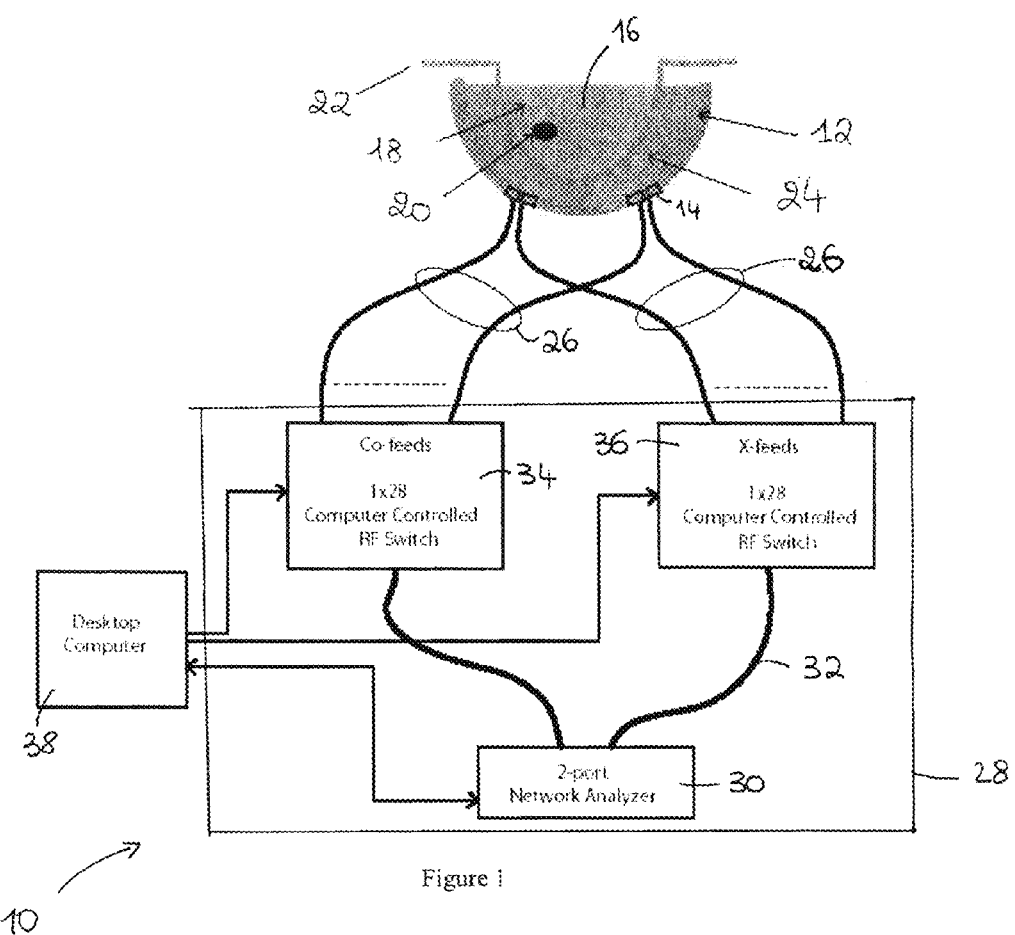
FIG. 1 is a schematic diagram of a microwave imaging system for breast cancer detection in accordance with an illustrative embodiment of the present invention.

Referring to FIG. 1, and in accordance with an illustrative embodiment of the present invention, a system for breast cancer detection using microwave imaging, generally referred to using the reference numeral 10, will now be described. The system comprises a three-dimensional (3D) spherical dielectric support/radome 12 with through slits for inserting a plurality of scanning elements such as miniaturized antennas 14 that form the illustrated spherical 3D card scanner array. The support 12 as disclosed is illustratively an enclosure used to protect the antennas 14 from the effects of environmental exposure and comprises a hollow bowl like portion designed to fit optimally around the breast 16. In this regard, a diseased breast 16 may be modelled as a fat phantom 18 into which is incorporated a tumour phantom 20 and covered with a skin phantom 22. A liquid filled matching bag 24 is placed between the support 12 and the breast 16 to provide for better energy coupling between the array of antennas 14 and the breast 16. Coaxial cables 26 are used to connect the antennas 14 to an electronic unit 28.

Still referring to FIG. 1, the electronic unit 28 illustratively comprises a two-port network analyzer 30 acting as a microwave trans-receiving unit connected through radio frequency (RF) cables 32 to a Co-channel switching network 34 and a X-channel (cross-channel) switching network 36. Each switching network is controlled by a desktop computer 38, which is also connected to the two-port network analyzer 30. The coaxial cables 26 thus connect antennas 14 to the electronic unit 28 via the switching networks 34 and 36. Alternatively, each antenna 14 may illustratively have its own trans-receiving unit. However, depending on the technology used, this alternative may be more expensive than the one described herein above.

Still referring to FIG. 1, the antennas 14, which are retained within the support 12, are used to illuminate the breast 16 by radiating broad bandwidth pulses that propagate into the tissue. The focal point of the beam scans different volumes within the breast 16 and detects the difference between the dielectric properties of a tumour 20 and that of the healthy tissue surrounding the tumour 20. Indeed, as discussed above tumours 20 have a greater dielectric constant than the otherwise normal fat tissue 18 adjacent the tumour 20, and as a result the microwaves incident on the tumour 20 are scattered with an energy which is characteristically larger than the energy of microwaves scattered by other scattering sources. The backscattered microwaves are then collected by the antennas 14 and their relative arrival times and amplitudes analysed using image formation algorithms (described further herein below) to determine the location and form an image of the scatterer, i.e. that is the tumour 20 in the current illustrative example. The antennas 14 are thus used for both transmission and reception of the microwave signal. Illustratively, performance can be improved and design requirements simplified if antennas 14 are arranged in pairs. In this case, one antenna (Co-antenna) illuminates the breast 16 and collects the co-polarized (same transmit and receive polarizations) backscatter returns and the other antenna (Cross- or X-antenna), which is orthogonal to the Co-antenna, collects the cross-polarized (orthogonal transmit and receive polarizations) backscatter returns. The Co-channel and X-channel switching networks 34 and 36 separate and sequentially connect the antennas 14 by each cycling the signal between one of the two ports of the network analyzer 30 and one of the Co- or X-antennas 14. As a result, one of the Co-antennas is connected to one port of the network analyzer 30, while an X-antenna is connected to the other port at any one instance. One port of the network analyzer 30 is therefore used as a trans-receiving port while the other is in receiving mode, allowing for both co- and cross-polarization backscatter responses from the tumour 20 to be recorded.

Figure 2:
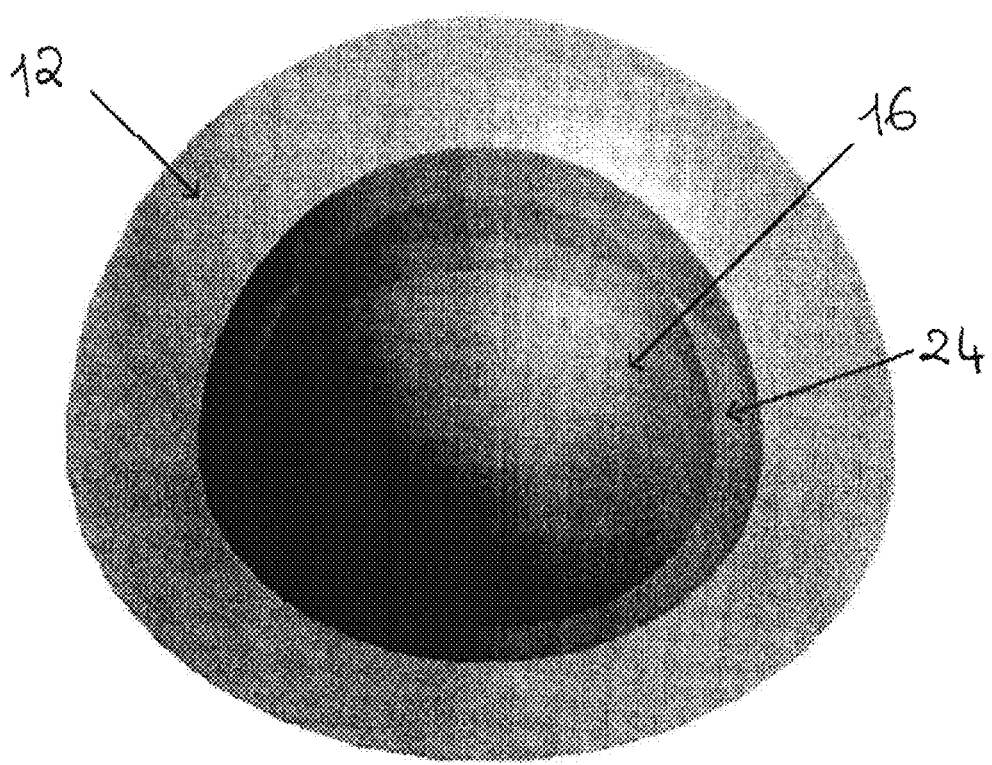
FIG. 2 is a schematic diagram of a dielectric support and matching liquid bag surrounding breast tissue in accordance with an illustrative embodiment of the present invention.
Figure 3:
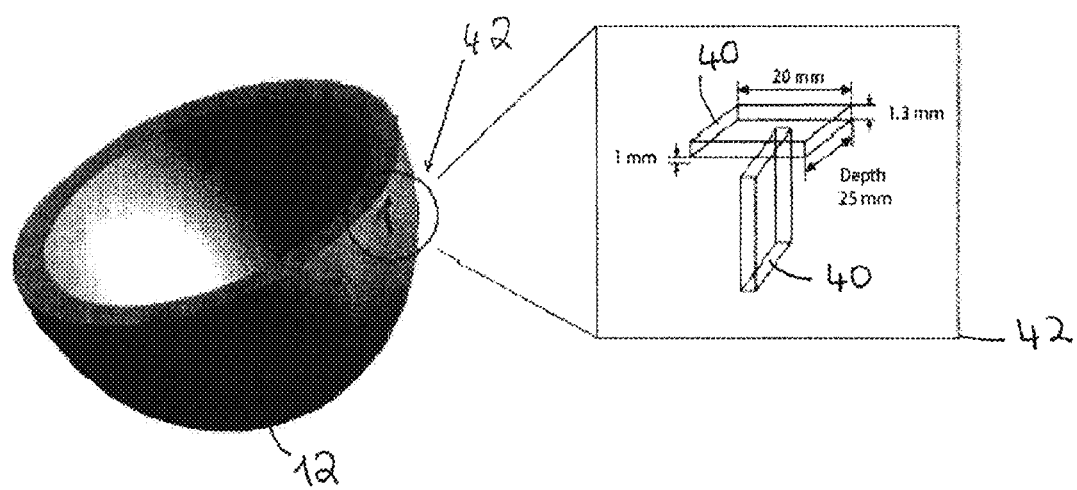
FIG. 3 is a schematic diagram of a dielectric support with a cut-through slit for inserting an antenna pair in accordance with an illustrative embodiment of the present invention.

Referring now to FIGS. 2 and 3 in addition to FIG. 1, the dielectric support 12, which is cast from a suitable material to form a partially hollow halfsphere, illustratively has a dielectric constant equal to 10.2, which falls in the range close to that of dielectric constants of biological materials. It should fit optimally around the breast 16, especially where it touches the patient's chest and could be fixed to it with an easily removable brassiere-like holder. Proper selection of the coupling medium that fills the matching liquid bag 24 typically improves the resolution of reconstructed images by minimizing air gaps and unwanted reflections of microwave energy. As shown in FIG. 3, through slits 40 are arranged in pairs orthogonal to one another to form a T-shaped aperture 42 machined in the support 12. Two cross-polarized antennas 14, which are illustratively etched on a thin resilient card like substrate such as a Printed Circuit Board (PCB) or the like, are inserted into each slit 40 of the T-shaped aperture 42. For sake of simplicity and illustration, only one T-shaped aperture 42 is shown in FIG. 3, although it should be understood that typically a number of such T-shaped apertures as in 42 are cast into the support 12 and into which antennas as in 14 are inserted thereby forming an array of antennas 14. As mentioned herein above, this arrangement allows for detection of both the co- and cross-polarization backscatter responses from the tumour 20. Moreover, this card-array configuration makes each antenna 14 replaceable so that a potentially non-functioning antenna 14 may be conveniently removed from the slit 40 it was initially inserted into and replaced by a functioning antenna.

Figure 4:
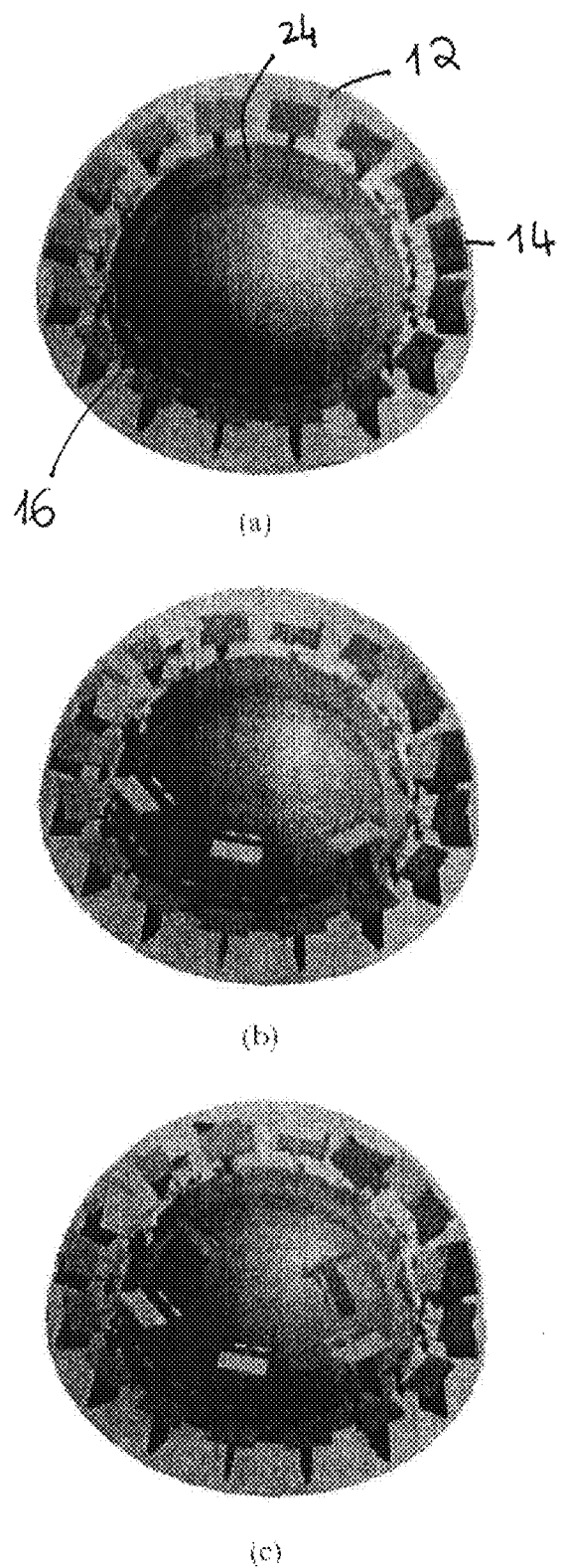
FIG. 4 is a schematic diagram of arrangements of antennas distributed around the dielectric support to form a card array in accordance with an illustrative embodiment of the present invention.
Figure 5:
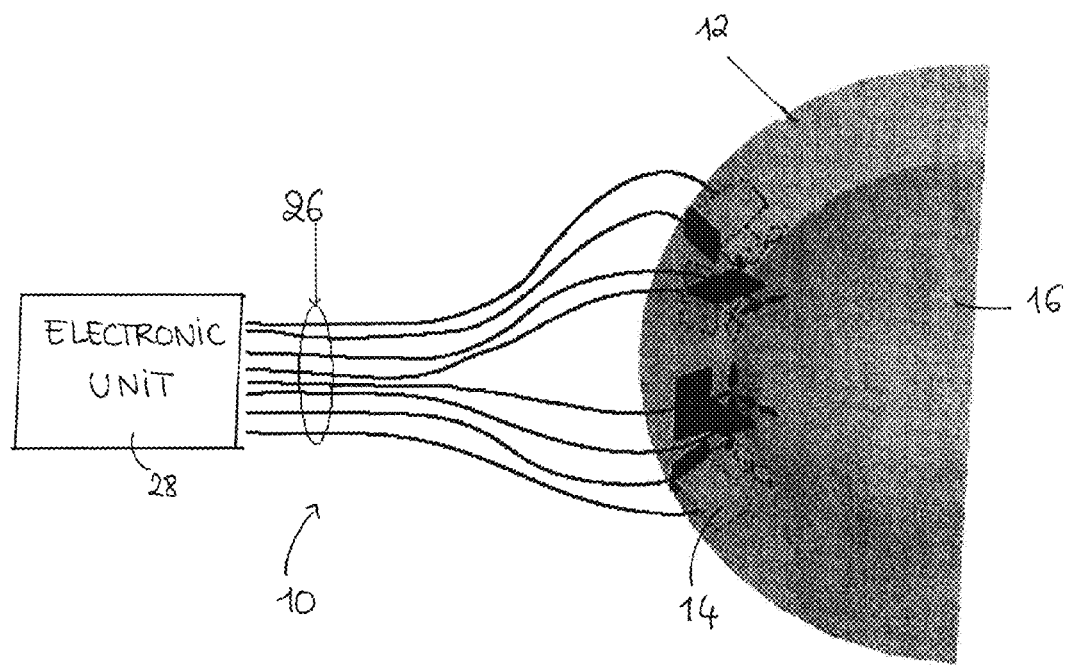
FIG. 5 is a schematic diagram of a dielectric support hosting antennas connected to an electronic unit in accordance with an illustrative embodiment of the present invention.

Referring now to FIGS. 4 and 5, the small size of the antennas 14, their planar structure and feeding mechanism, as discussed further herein below, allows for the configuration of a large number of antennas 14 into a three-dimensional (3D) antenna array adapted for detection and imaging of small tumours 20. Indeed, the use of more antennas 14 allows for generation of a more focused beam and as a result higher resolution and more precise detection of tumours 20. As a result, an antenna array may be formed from different arrangements of a number of miniaturized antennas 14 without departing from the scope of the present invention. For example, FIG. 4 (a) shows a first ring of 32 antennas 14 arranged orthogonally as 16 T-shaped "cells", or pairs, and distributed laterally around the circumference of the support 12. In FIG. 4 (b), a second ring of eight (8) T-shaped cells is distributed laterally around the support 12 adjacent the first ring to form a second annular array, while in FIG. 4 (c), an additional four (4) more T-shaped cells are added in the same manner to the structure of FIG. 4 (b) to form an annular array. As shown in detailed in FIG. 5 and as discussed briefly hereinabove, the coaxial cables 26 connect the electronic unit 28 to each antenna 14 of a given T-shaped cell. For sake of clarity, only the last annular array of antennas 14 is shown in FIG. 5.

Figure 6:
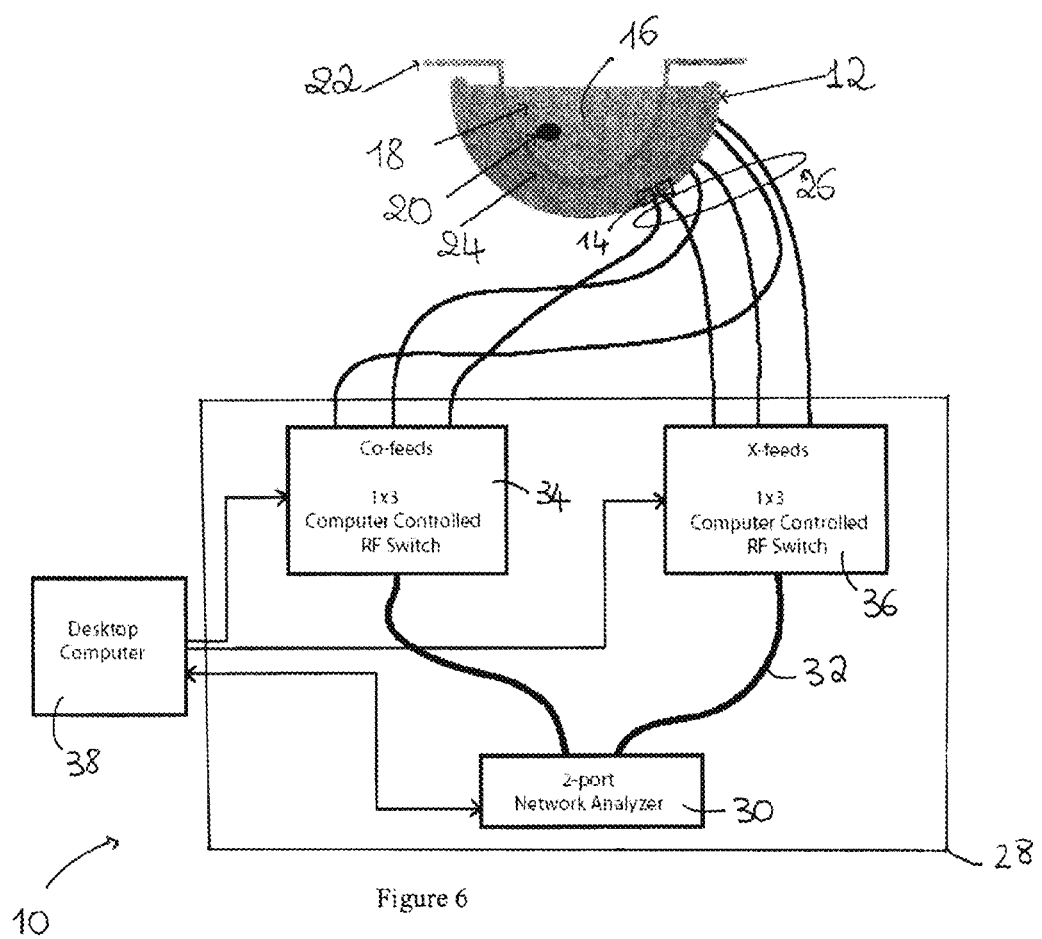
FIG. 6 is a schematic diagram of a mechanically rotated microwave imaging system for breast cancer detection in accordance with another illustrative embodiment of the present invention.
Figure 7:
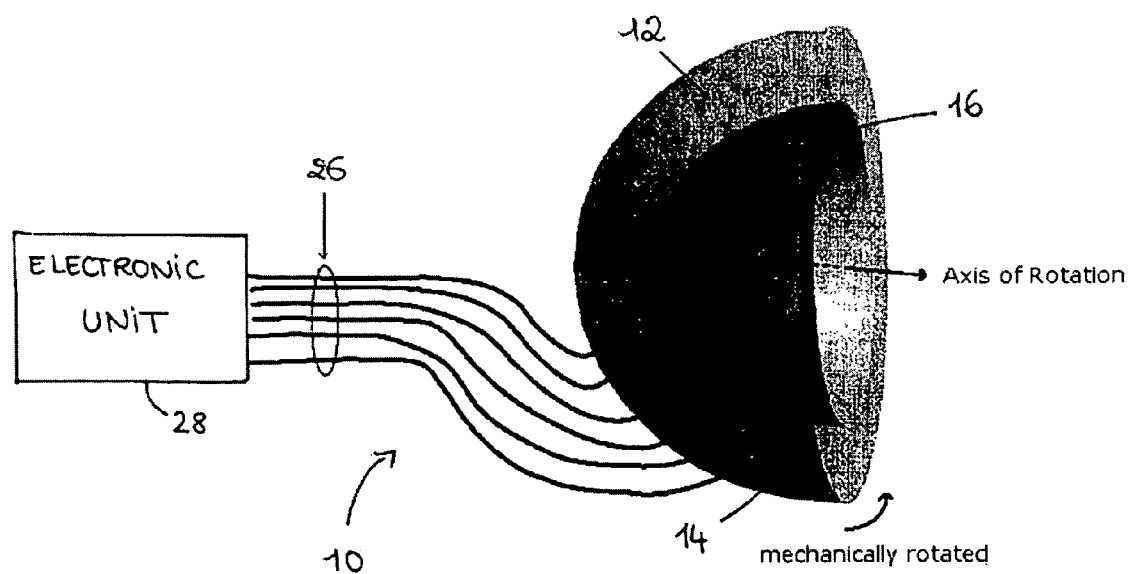
FIG. 7 is a schematic diagram of a mechanically rotated dielectric support of FIG. 6 hosting antennas connected to an electronic unit in accordance with another illustrative embodiment of the present invention.

Referring now to FIGS. 6 and 7, in an alternative embodiment of the present invention, a fewer number of antennas 14 can be positioned on an arc on the support 12, which is then mechanically rotated around the breast. The breast is therefore scanned at various locations and measurements are taken for specific angular positions of the antennas 14. In this case, the support 12 illustratively comprises two layers (not shown) with the inside layer remaining fixed on the patient's breast while the upper layer rotates along a predetermined axis of rotation. This method allows for simplified data acquisition system when compared to the electronic steered array method described herein above. Indeed, the number of antennas 14 and the complex RF switching network is reduced substantially, though at the expense of the addition of a simple mechanical rotation system.

Referring back to FIGS. 1 and 6, after a time delay corresponding to the round trip distance between the antennas 14 and the tumour 20, the backscattered microwaves, which follow an excitation signal, are collected by the antennas 14. In this regard, although only a given one of the antennas 14 may emit microwave pulses during a given period of time, typically all of the antennas as 14 receive backscattered microwaves and relay these to the computer 38 for recording and further processing. Additionally, when each antenna has its own trans-receiving unit, it is possible that several of these antennas to transmit a focused signal to a specific location inside the breast, providing a better penetration capabilities of large breasts for examples The recorded signals typically exhibit early and late time content, which is analysed by image formation algorithms implemented by the computer 38 to determine the location of the tumour 20 and form a corresponding image. While early time content is dominated by the incident pulse, reflections from the skin and residual reverberations, late time content contains tumour backscatter and backscatter due to clutter. Signal processing is thus necessary to reduce the effect of the reflection artefact response on the received image data, i.e. the early time content, which is typically orders of magnitude greater than the tumour response, and selectively enhance the tumour response while suppressing clutter. This process will ensure reliable detection of the tumour 20 in the images, which are reconstructed from the post-processed signals.

Additionally, in the present illustrative embodiment processing of the received backscattered microwaves is aided by the rotational symmetry of the miniaturized antennas 14 within the scanner array. Indeed, referring to FIG. 4, the miniaturized antennas 14 of each layer are positioned in a rotationally symmetric manner. This feature can be taken advantage of to remove the early time response via a simple averaging process. In a scanner array of N antennas, when a first antenna 14 is excited to emit a series of microwave pulses, a set of N backscatter signals is recorded. When a second antenna as in 14 is excited a second set of N backscatter signals is recorded. Given the rotational symmetry of the canner array, cyclic rotation is used to align the early time artefact in all recorded signals, that is the first set of N backscatter signals is aligned with the second set of N backscatter signals and so on. As the tumor response is not aligned, by averaging the aligned signals, a set of N signals that mostly contain the early time response is generated. In this way the tumor response in the signals is reduced by a factor of N.

Large reflection artefacts, such as the energy reflected from the ends of the antenna 14, from the skin-breast interface or from blood vessels, are removed by subtracting them from the antenna signals to create artefact free data prior to performing tumour detection. Integration of the calibrated backscatter signals then follows to ensure that they have a maximum value at their centre point, further allowing coherent summation of local maxima through time-shifting. Compensation for radial spreading (i.e. a decrease in amplitude as the wave signal expands) and path loss (i.e. a reduction in the strength of the signal due to its propagation through lossy tissue) may also be implemented. The reconstructed image is then created by focusing the calibrated and integrated signals at specific points in the breast, summing contributions from each processed waveform and further computing the intensity of each pixel in the reconstructed image sum for a corresponding focal point.

The above-mentioned algorithms may be modified to tailor to other types of microwave imaging applications, for which the antenna 14 could be used, such as through wall imaging and ground penetrating radar systems. These applications could further benefit from the development of complete portable systems stemming from the small size of the antennas 14, which allows for their incorporation into small units.

Figure 8:
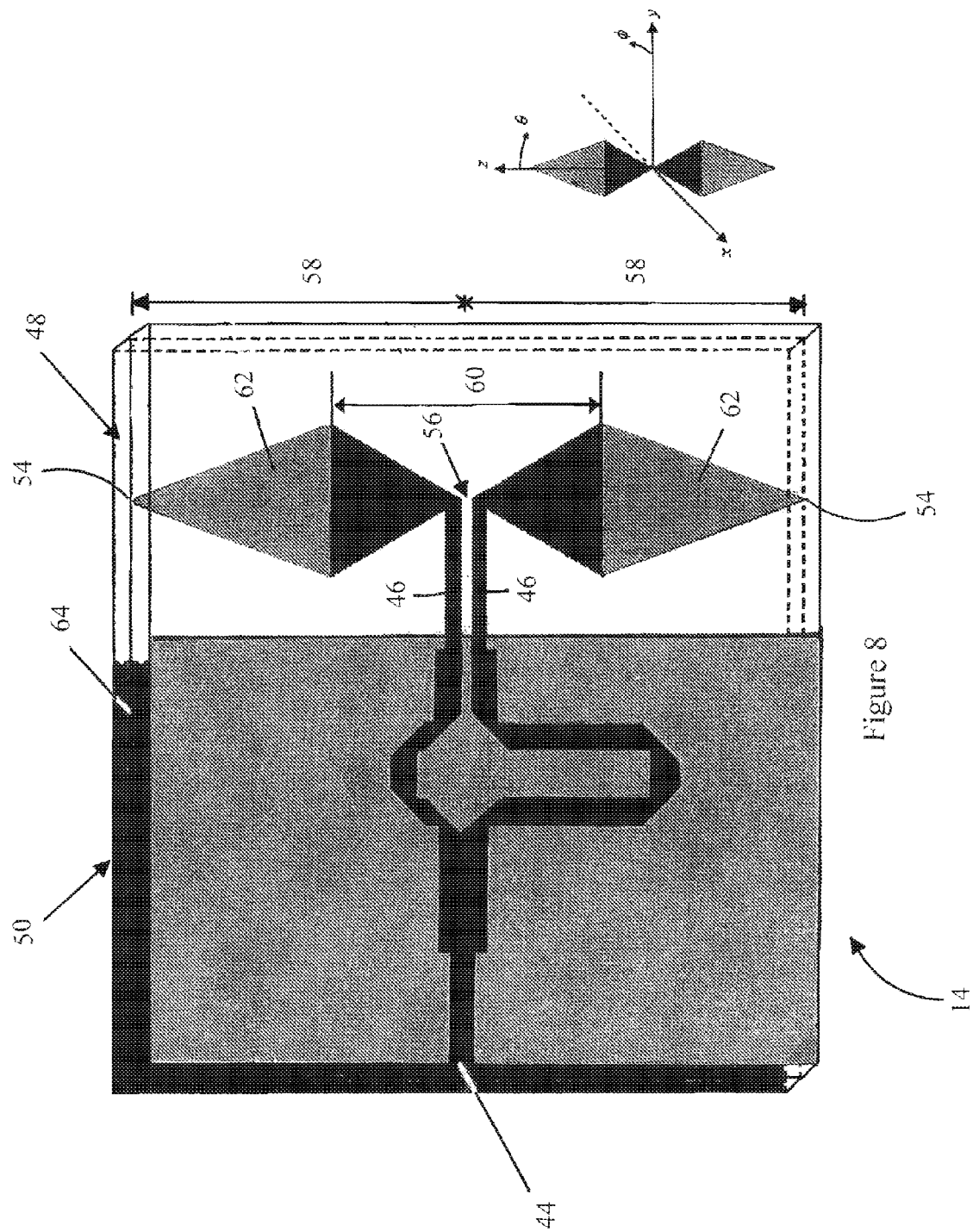
FIG. 8 is a schematic diagram of the geometry of a miniaturized antenna in accordance with an illustrative embodiment of the present invention.
Figure 9:
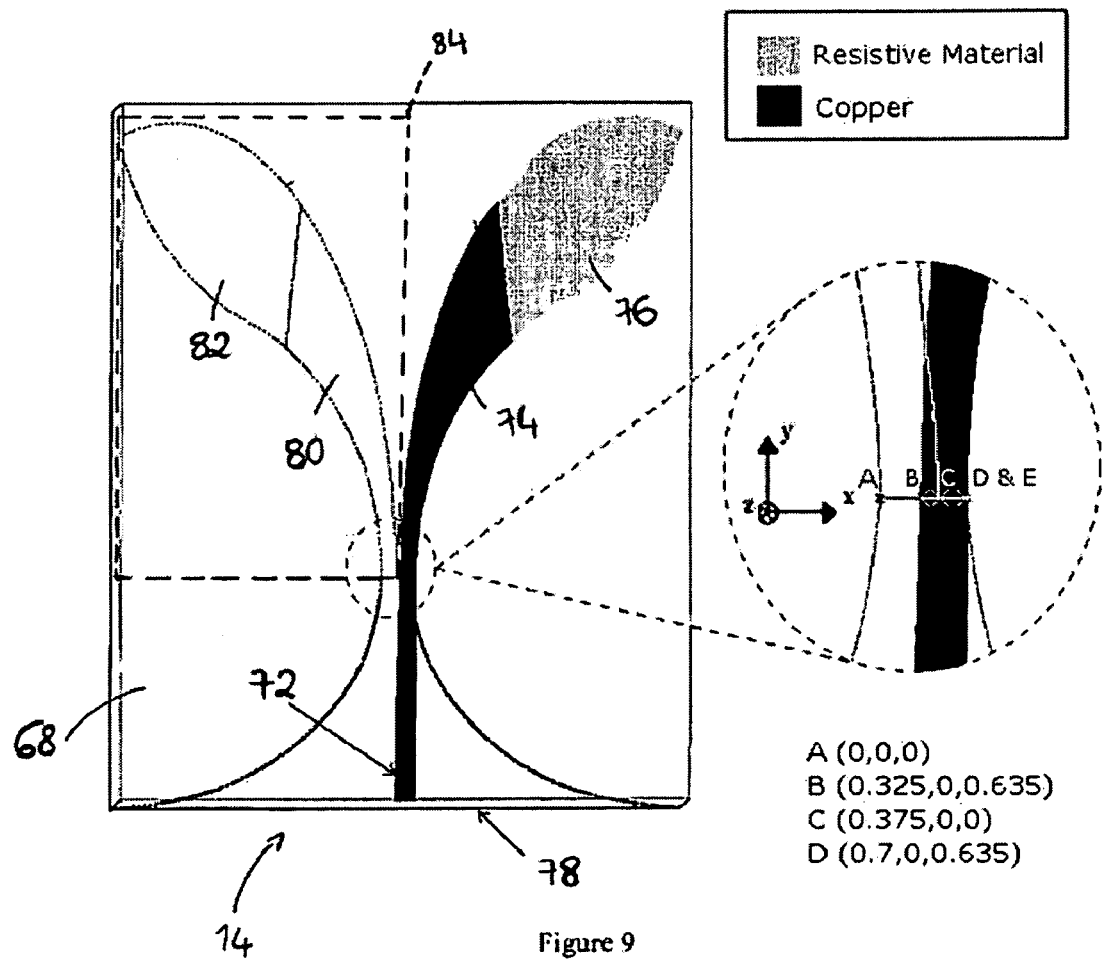
FIG. 9 is a schematic diagram of the geometry of a miniaturized antenna in accordance with another illustrative embodiment of the present invention.

Referring now to FIGS. 8 and 9 in addition to FIG. 1, the antennas 14 should be compact for easy mounting and integration with electronic circuits, as well as fabrication of arrays. In order to ensure efficient power transfer, reflections should also be avoided by matching the antenna impedance to that of the transmission line, which connects the antennas 14 to other devices, illustratively the electronic unit 28 of the present invention. For this purpose, balanced-to-unbalanced transformers (balun) are used to connect the antennas 14, which are typically balanced devices, to unbalanced transmission lines such as the coaxial cables 26. Since small targets are of interest, it is also desirable that the antennas 14 radiate excitation pulses with a minimal degree of distortion and loss. It would therefore be desirable for them to only produce low levels of edge reflections to avoid masking of the targets and corruption of the transmitted signal. Moreover, as known in the art, in order to achieve the best resolution of the reconstructed image, the microwave pulse radiated in microwave imaging applications should be relatively short, i.e. about 100 ps, and thus have a wideband frequency content, typically from 0 to 20 GHz with significant energy in the frequency range of 1 to 10 GHz. As a result, it is desirable to use wideband antennas, which will properly focus the microwave pulses towards the target and collect the back-scattered energy, thus ensuring proper transmission of the microwave signal.

Due to their simplicity and broadband performance, bowtie antennas are often used in microwave imaging applications. Indeed, as tapering of antenna components increases bandwidth, bowtie antennas comprise two similar-shape triangular elements, which are responsible for the antenna's broadband behaviour. Nevertheless, antenna ringing remains a disadvantage of bowtie antennas along with low directivity, and unstable characteristic impedance. Antenna ringing is characterized by the fact that the bowtie antenna doesn't only radiate during the duration of the excitation pulse but also after the pulse has died down due to multiple reflections that occur between the end of the bowtie antenna wings and the excitation point. Further, a pulse emitted through a feed line located at the center of the bowtie would experience reflections off the antenna ends. These reflections could overlap in time with the backscatter returns from a possible tumour, and therefore would corrupt the trans-received signals and jeopardize signal integrity and proper broadband antenna behaviour. This effect is illustratively reduced by resistively loading or terminating the antenna, i.e. connecting load resistors at the bowtie wing ends to suppress reflections. Load resistors are selected to match the antenna impedance to the ground impedance, thus providing for efficient energy transfer from the antenna to the ground and allowing resistively loaded antennas to exhibit broader bandwidth.

Antennas may be resistively loaded in several ways and illustratively, through the use of a graded resistance method, in which changes in resistance are induced by the antenna geometry. Still referring to FIGS. 8 and 9, the antennas 14 are designed to be microstrip-fed planar antennas loaded with material of constant surface resistance in order to minimize off-end reflections. Microstrip antennas are typically manufactured on Printed Circuit Board (PCB) as metallic patches over a dielectric substrate, which resides on top of a ground plane. Microstrip antennas offer the advantages of being inexpensive, durable, lightweight, and having a low profile conformable to various surfaces. Unlike variable resistive loaded antennas, which are difficult to manufacture, microstrip antennas with constant resistive loading use standard PCB manufacturing processes with embedded technologies, allowing for antennas 14 that are easier to manufacture in a repeatable and accurate manner. Indeed, as the resistance at a given point along a conductor is related to its cross-sectional area and the thickness of the conductive material laminated or printed onto the PCB accurately controlled using currently available technology, resistance can be accurately controlled. As mentioned above, although the antennas 14 are implemented as part of a biological sensing (breast cancer detection) system for the sake of illustration, it should be understood that the ultra-compact and planar nature of both designs described herein below makes the antennas 14 suitable for a wide range of other microwave imaging applications such as through wall imaging and ground penetrating radars.

Figure 10:
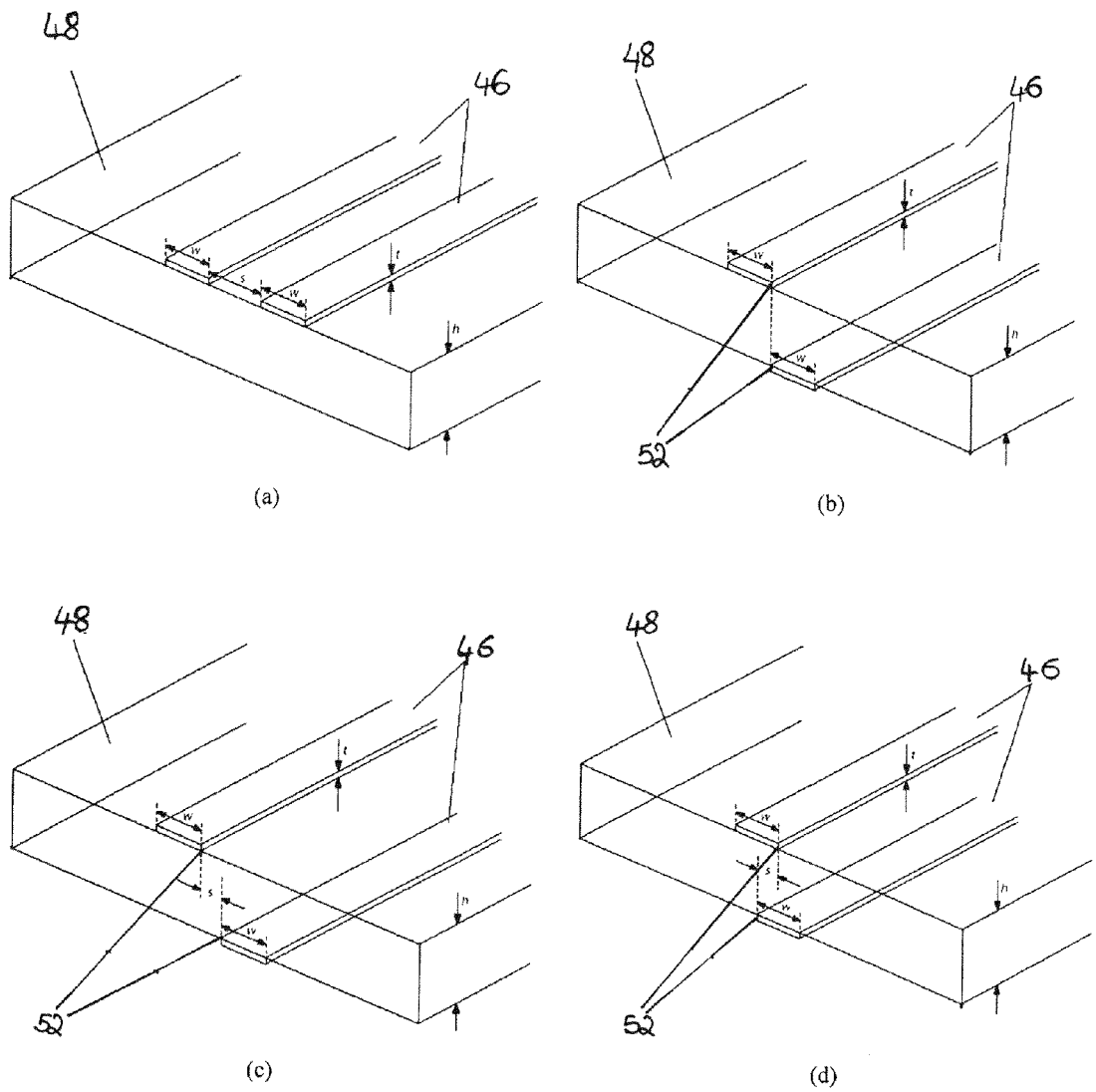
FIGS. 10(a) through 10(d) provide a schematic diagram of possible configurations for the transmission line of an antenna in accordance with an illustrative embodiment of the present invention.

Referring now to FIGS. 10(a) through 10(d) in addition to FIG. 8, the design of the radiating elements of the antenna 14 illustratively begins with the design of the feed 44, and more specifically of its two (2) conductive strips 46, which carry the signal to and from the antenna 14 and are designed with a pre-determined characteristic impedance. This characteristic impedance depends on a variety of parameters, including the relative permittivity $\in_{rs}$ of the dielectric substrate 48, the relative permittivity $\in_{rb}$ of the background material 50, the height h of the dielectric substrate 48, the width W of each conducting strip 46, the conducting strip thickness t, and the conducting strip separation S. Depending on whether the antenna 14 is intended to be coplanar, i.e. the conducting strips 46 lie on top of the dielectric substrate 48 in the same geometric plane, or antipodal, i.e. the conducting strips 46 lie on substantially parallel geometric planes on either side of the dielectric substrate 48, the initial transmission line design will either have a Coplanar Strip (CPS) or Antipodal Strip (APS) configuration, as shown in FIG. 10. As a result, the final antenna will be either a Tapered Coplanar Strip Antenna (TCPSA) or a Tapered Antipodal Strip Antenna (TAPSA). The choice between coplanar or antipodal antenna depends on system requirements such as the characteristic impedance of the antenna, the minimum acceptable cross-polarization, material availability and cost, or design of the matching balun structure. In addition, although it typically has higher cross-polarization than its planar counterpart, it is easier to design a broadband matching feed for the antipodal structure and it may therefore be desirable to design an antipodal antenna. A typical CPS feed structure is illustratively shown in FIG. 10(a), while possible variations in the APS feed structure are shown in FIG. 10(b), 10(c), and 10(d). While FIG. 10(b) shows an APS configuration with even strip edges 52, FIG. 10(c) shows an APS configuration with separated strip edges 52, and FIG. 10(d) shows an APS configuration with overlapping strip edges 52. Once the desired feed configuration (CPS or APS) has been implemented, the remaining antenna elements may be designed, as described further herein below.

A miniaturized antenna 14 according to a first illustrative embodiment of the present invention is shown in FIG. 8. The antenna 14, which has a CPS feed configuration and a combined bowtie and inverted-bowtie geometry, with its width tapered along its longitudinal axis towards its distal ends 54 starting from the bowtie end, where it is wide. The antenna 14 has an apex 56 and radiating elements 58, which comprise the bowtie-like metallic section 60 connected to two tapered-down segments 62 (forming inverted-bowtie-like sections on each side of the bowtie-like section 60), which act as a constant resistive loading. With a constant surface resistance, an increase in resistance per unit length can be experienced by the signal as it travels towards the antenna ends 54 along a longitudinal path. The surface resistance of each radiating element 58 of the antenna 14 varies from a relatively low value near the apex 56 to a very large value near the distal end 54. The gradient of resistance per unit length can be controlled by careful design of the taper, for example the resistance can be increased more rapidly by employing a different taper geometry, such as an exponential one. In addition to the use of constant-value resistance, this design has the advantage of resulting in an antenna 14 having a compact size, which eases its implementation into an antenna array. Illustratively, the antenna 14 is printed or laminated onto a substrate 48 of dielectric constant equal to 10.2, for example using suitable printing or etching process, which is close to the real part of the relative permittivity of the biological material to be irradiated. The antenna 14 is therefore considered as being immersed in a lossless medium with dielectric properties similar to those of normal fatty tissue. A resistive layer 64 is placed over one outer dielectric layer of the feed 44 to reduce its radiation and resonance. The ground plane 50 is placed on the other outer dielectric surface, on the opposite side of the feed plane.

Although the antenna 14 shown in FIG. 8 and described herein above exhibits increased bandwidth (illustratively between 1 and 11 GHz with a central frequency of 6 GHz as suggested for pulsed breast cancer imaging) compared to a typical bowtie antenna, the parasitic resistive loading over the feed 44 causes increased resistive losses, resulting in low radiation efficiency. Careful design of the transition region between the antenna feed 44 and the radiating elements 58 could eliminate the need of the parasitic resistive loading and result in improved antenna performance. Indeed, the transition region is responsible for connecting as well as decoupling the highly capacitive feed structure 44 to the inductive radiating elements 58. As known in the art, the transition region should prevent a sharp discontinuity (and thus the resulting pulse distortion) between the feed 44 and radiating elements 58. A properly designed transition region will also convert the unbalanced feed 44 into a balanced structure that can be connected to the radiating elements 58 of the antenna 14. For this purpose, it is desirable for the transition region to be smooth and slowly tapered to develop into the radiating elements 58. The taper, which constitutes a critical aspect of the antenna design, should be gradual and smooth to avoid significant discontinuities, which will cause reflections and result in a distorted pulse-shape.

Referring now to FIGS. 9 and 11(a) through 11(e) in addition to FIG. 8, in order to properly design the tapered transition region of the antenna 14 shown in FIG. 8, each conducting strip 46 of the initial transmission line design is tapered, as illustrated in FIGS. 11(a) through 11(e), to introduce parameterization curves with different taper profiles, leading to the optimised antenna design of FIG. 9. As will be apparent to a person skilled in the art, these taper profiles may be elliptical, exponential, or any function of a similar form, as well as a combination of different functions, with some being linear for example. Still, as mentioned herein above, it is desirable for the curves to be as smooth as possible, i.e. have a continuous second order derivative at any joining point.

Figure 12:
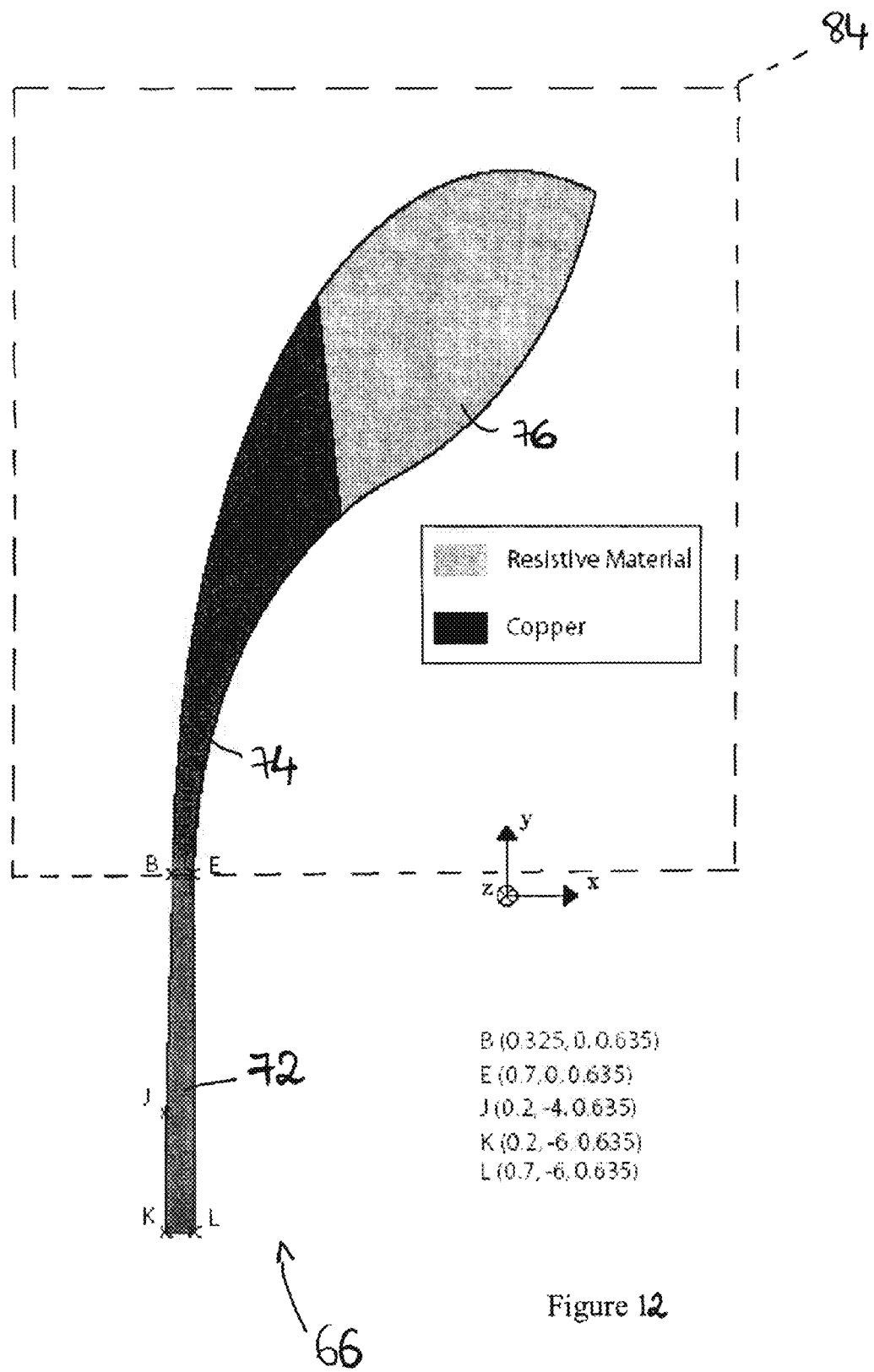
FIG. 12 is a top view of the top plane of the miniaturized antenna of FIG. 9 in accordance with an illustrative embodiment of the present invention.

Referring now to FIGS. 9, 12, 13, and 14, a TAPSA design for the miniaturized antenna 14 according to an alternative illustrative embodiment of the present invention is shown. To achieve the smooth and gradual transitions in the shape and best design the taper of the antenna 14, ellipses with different-length minor and major axes were illustratively investigated. The antenna 14, which has a continuous shape, consists of a top layer 66, a dielectric substrate 68, and a bottom layer 70. As seen in FIG. 12, the top layer 66 comprises a linearly tapered microstrip feed 72 connected to an elliptical radiating element 74, illustratively fabricated from a thin copper laminate on top of the dielectric substrate 68, and an elliptical tapered resistive section 76, which serves as a partially radiating and partially dissipating element, illustratively fabricated from a resistive material.

Referring to FIG. 13(a), the bottom layer 70 consists of an elliptical tapered section forming the ground plane (or balun) 78 along with radiating/dissipating elements 80 and 82, which are similar in shape, albeit mirrored, to the elements 74 and 76 of the top layer 66. The antenna radiating elements 84 are therefore composed of metallic elements 74 and 80 and resistive sections 76 and 82 of the top and bottom layers 66 and 70.

Figure 13:
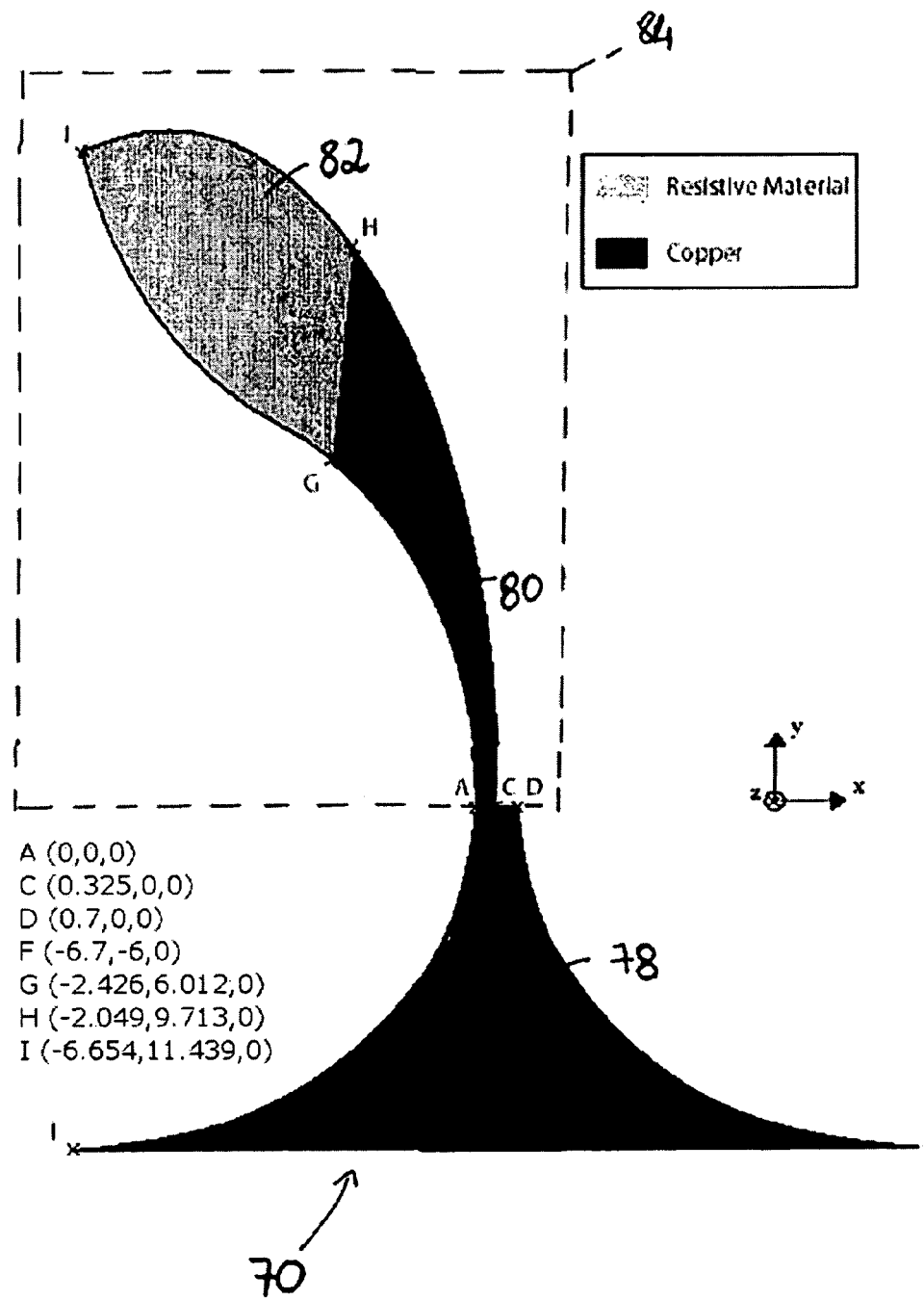
FIG. 13(a) is a top view of the bottom plane of the miniaturized antenna of FIG. 9 in accordance with an illustrative embodiment of the present invention.
FIG. 13(b) is a top view of a miniaturized antenna in accordance with an alternative illustrative embodiment of the present invention.
Figure 13B:
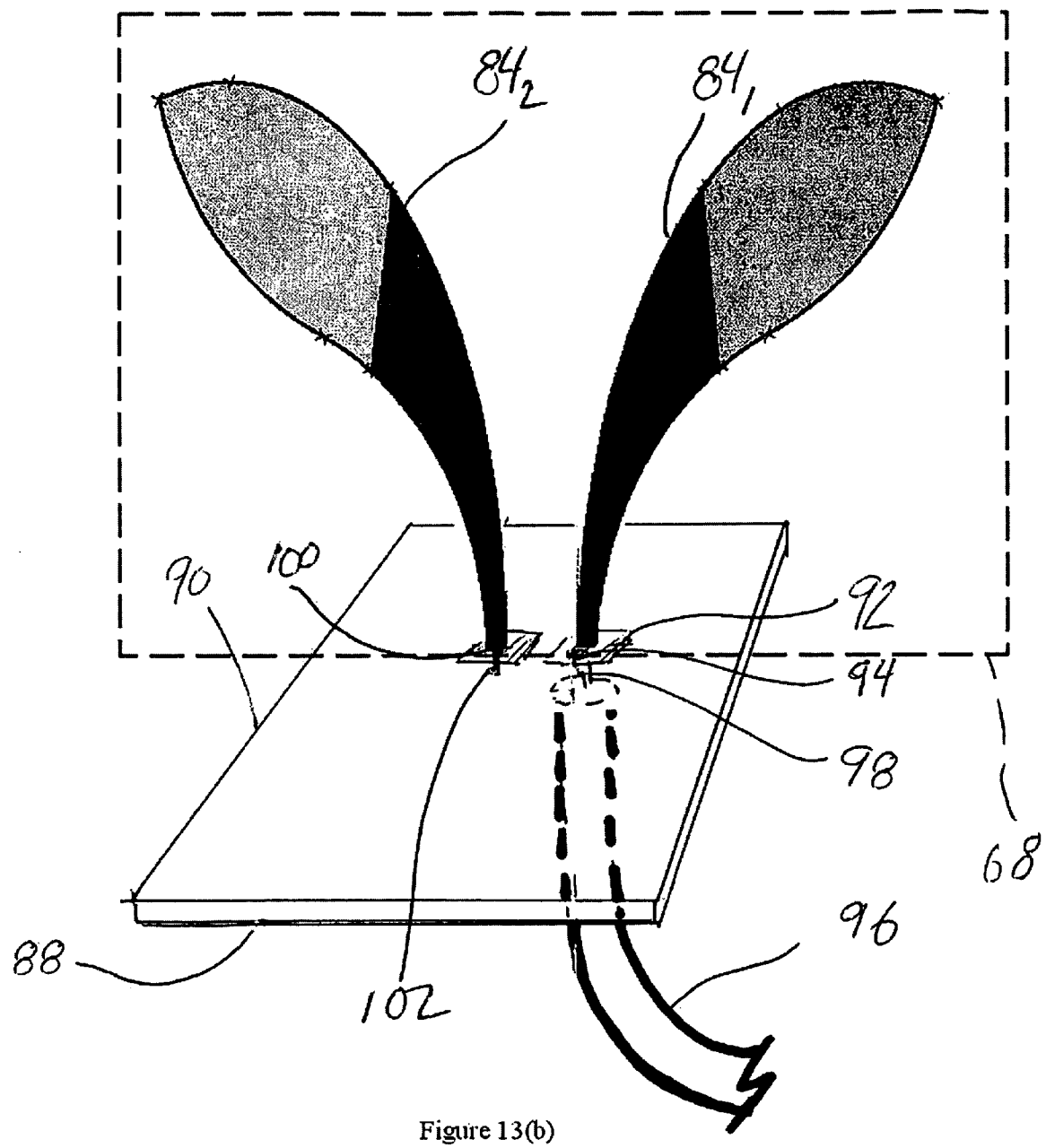
Figure 14:
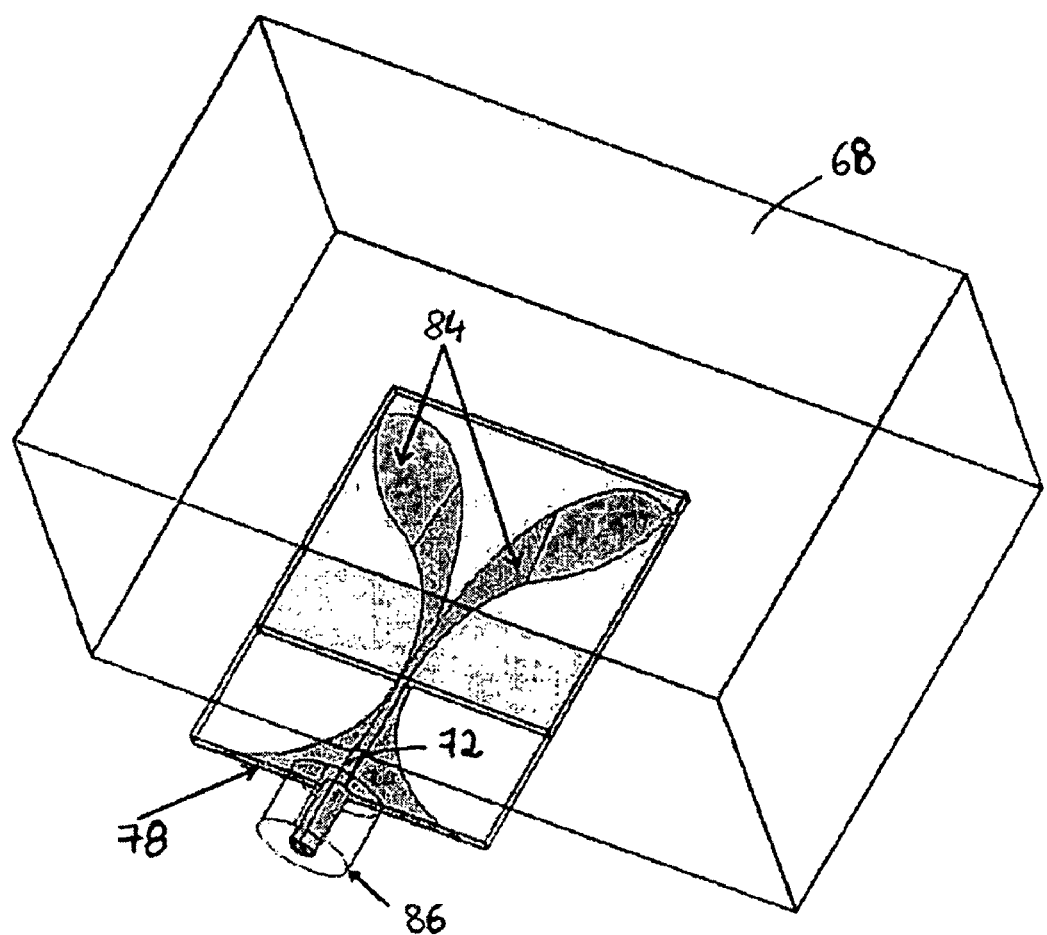
FIG. 14 is a schematic diagram of the antenna of FIG. 9 immersed as a card in a matching medium in accordance with an illustrative embodiment of the present invention.

Referring now to FIG. 13(b), in an alternative embodiment, the radiating elements 84 can be fed through a ground plane 88 where radiating elements 84 are perpendicular to the ground plane 88. In this configuration, the radiating elements as in $84_1$, $84_2$ are positioned perpendicular to a second substrate 90 and secured, typically to a small pad 92 of conductive material, for example through the use of conductive solder or the like (not shown). A hole 94 positioned immediately adjacent the point of attachment between radiating element 84 and second substrate 90 is machined or otherwise formed through the second substrate 90. A co-axial connector 96 is positioned with its outer shield connected to the ground plane 88. The central conductor 98 of the coaxial connector 96 passes through the hole 94 without coming into contact with the ground plane 88 and interconnected with a first one of the radiating elements $84_1$, for example using conductive solder or the like. The second of the radiating elements $84_2$ is simply interconnected with the ground plane, for example by punching or otherwise forming a second hole 100 through the second substrate and provision of a conductor 102 there between, such as a small piece of conductive wire or solder, or the like. In this manner, the ground plane 88 itself acts as a balun. The disclosed alternative embodiment offers two advantages. Firstly, given that the ground plane 88 acts as a reflector, the assembly is more directed. Secondly, it is possible to place two pairs of radiating elements as in 84 in a co-located manner. In this regard, a second pair of radiating elements as in 84 is positioned at right angles to the first pair of radiating elements as in 84 with provision of a second hole as in 98 machined or otherwise formed in the substrate and a second co-axial connector as in 96.

Figure 11:
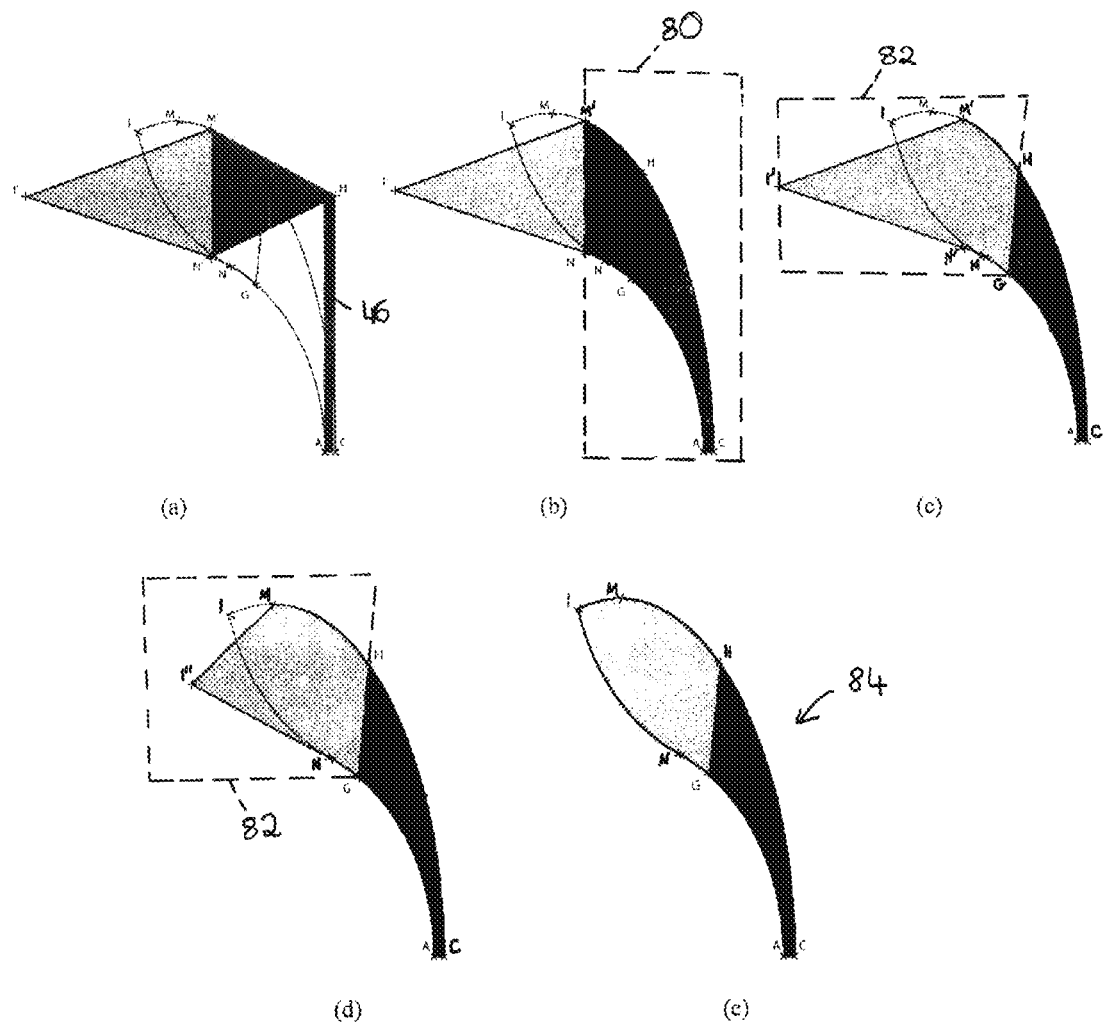
FIGS. 11(a) through (e) provide a schematic diagram of modifications implemented to modify the antenna geometry of FIG. 8 into that of FIG. 9 in accordance with an illustrative embodiment of the present invention.

Referring back to FIGS. 11(a) through 11(e) in addition to FIGS. 8 and 9, the sequence of modifications for transforming the antenna design of FIG. 8 into that of FIG. 9 is shown. From these modifications, an antenna 14 having an APS configuration is constructed and resistively loaded to achieve a broadband and compact design. Referring to FIGS. 11(a) and 11(b), the first evolved design of one arm of the antenna 14 results from a tapering of the conducting strip 46 of the initial transmission line design. Although the total width of the antenna 14, i.e. from point I' on one arm to point I' on the other arm (not shown), remains the same (illustratively 20 mm) in both FIGS. 11(a) and 11(b), the design of FIG. 11(b) leads to a metallic element 80 of larger area. The strong discontinuity at point M' where the current is still strong also leads to a lower centre frequency, illustratively around 5.5 GHz, and a bandwidth of 4.5 GHz to 6.5 GHz. FIG. 11(c) shows a second evolved design, in which the line M'N' is pushed back to become line HG. Although the antenna behaviour is significantly improved compared to the first evolved design of FIG.

11(b), the area of the resistive section 82 is larger, implying lower antenna efficiency. The antenna width is also the same as in the previous design. In the design shown in FIG. 11(d), there is illustrated an attempt to reduce the effect of discontinuity at point M' by pushing it further away on the CI curve up to point M. As a result, the lossy path, which the current travels before it intercepts a discontinuity, is made longer. In addition, the discontinuity at point N' is illustratively removed by pushing it slightly back to point N and extending the line in a tangent way at point N to intercept the line MI' at point I". The lossy resistive area 82 is therefore reduced and the total antenna width is reduced, illustratively to 16 mm. FIG. 11(e) shows the final design of the bottom layer radiating element 84 of FIG. 9, in which all discontinuities have been removed and the total antenna width is further reduced, illustratively to 14 mm. In FIG. 11(e), the discontinuity at point M is removed by extending the elliptic curve HM to point I where it is intercepted by another elliptical curve NI.

Figure 15A:
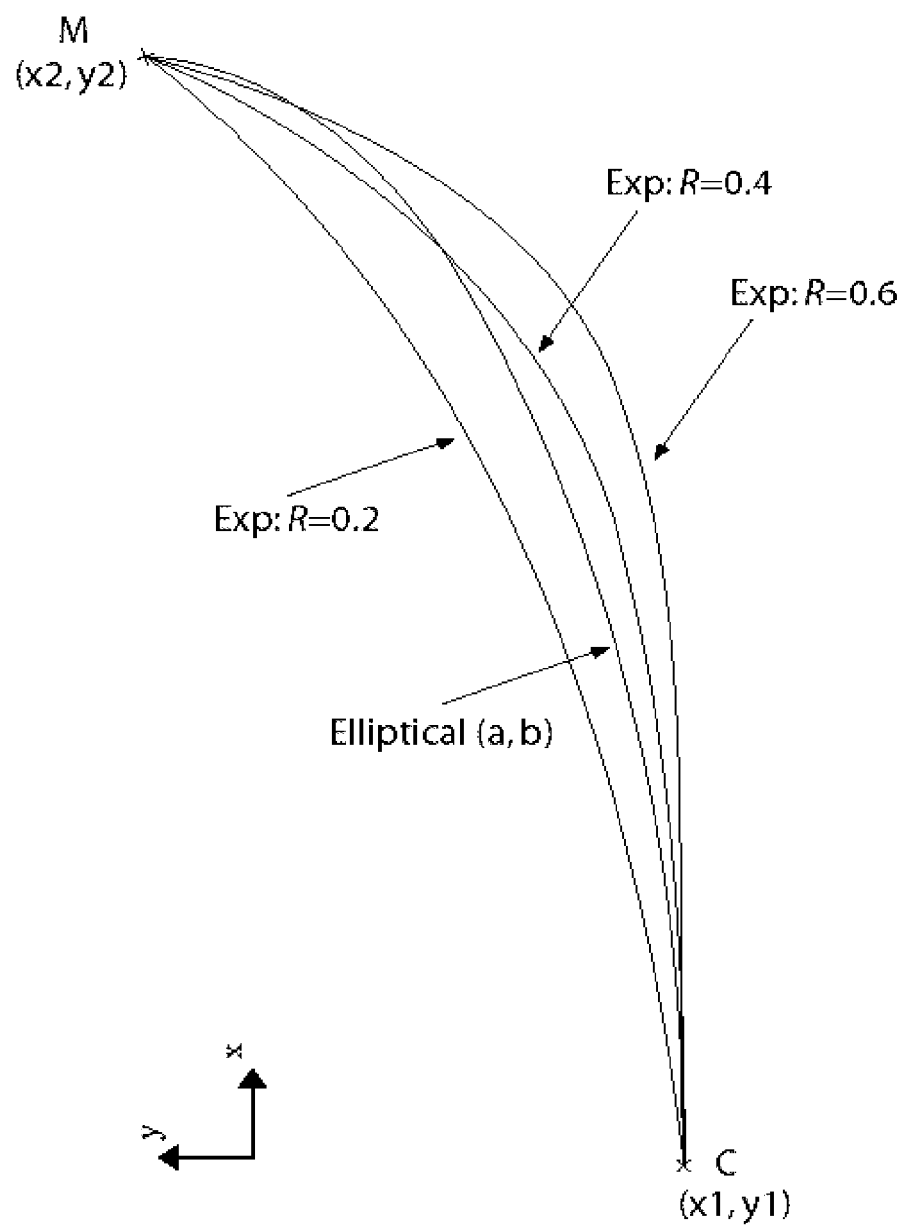
FIGS. 15(a) through (c) provide a schematic diagram of possible optimizations to the antenna geometry of FIG. 9 in accordance with an illustrative embodiment of the present invention.
Figure 15B:
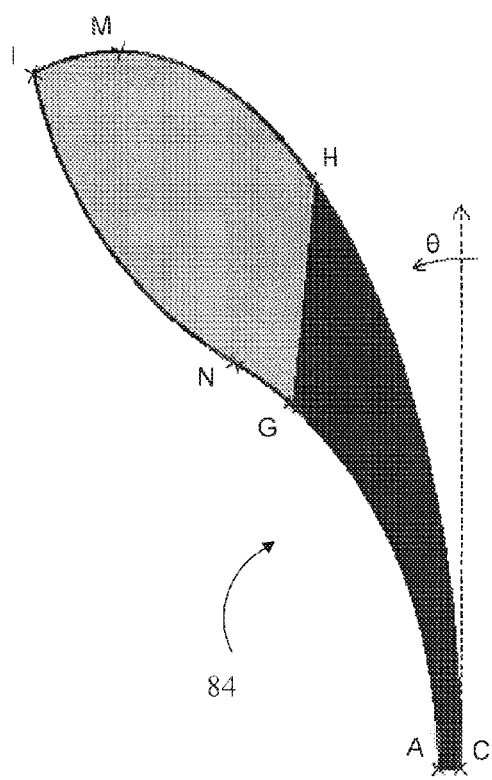
Figure 15C:
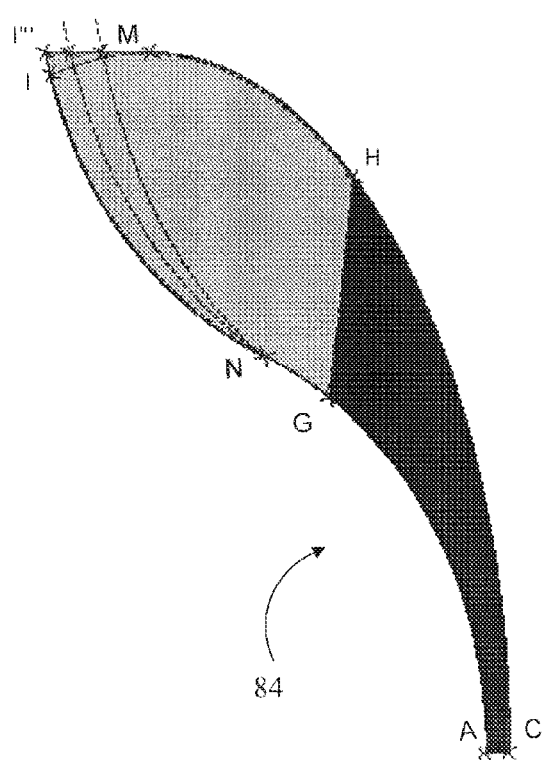

Referring now to FIGS. 15(a) through 15(c) in addition to FIG. 13, further optimization of the antenna 14 may be achieved by a variety of means. As mentioned herein above, different taper profiles other than elliptical (e.g. exponential) may be used, illustratively for curve MC of the radiating element 84, as shown in FIG. 15(a). In this case, the antenna performance will depend on the rate of the flare opening of the radiating element 84. Moreover, as seen on FIG. 15(b), a rotation of the radiating element 84 by a substantially small angle θ increases the total end opening of the flare, thus further reducing the lower cut-off frequency of the antenna 14. As shown in FIG. 15(c), smaller antenna width may also be achieved by modifying the tapering path, and more specifically the curve NI, of the radiating element 84.

The antenna geometry illustrated in FIG. 9 is simpler and shows an improved performance in terms of bandwidth, low pulse distortion, and ease of implementation compared to the earlier design described herein above. Another key advantage resides in the strong forward-region radiation pattern, which makes the antenna 14 a good candidate for cross-polarized card-array arrangements. Indeed, as described herein above and seen in FIG. 14 in addition to FIG. 3, the antennas 14 are printed on PCBs which are partially inserted into the slits 40 of the support 12, with the radiating elements 84 being fully immersed in the medium while the feed 72 and the balun 78 remain accessible thereby providing for coupling of the antenna 14 to electronic circuitry of the imaging system via waveguides 86 such as coaxial cables.

Although the present invention has been described hereinabove by way of specific embodiments thereof, it can be modified, without departing from the spirit and nature of the subject invention as defined in the appended claims.

The invention claimed is:

1. A micro strip antenna for terminating a transmission line comprising a pair of conductors, said antenna comprising:
a planar substrate fabricated from a dielectric material; and
a pair of like elements arranged in mirror image on said planar substrate, each of said elements comprising a dissipating portion on said planar substrate, and a radiating portion comprising an elongate conductive strip of a first constant thickness, said elongate conductive strip comprising first arcuate side edges mutually diverging between a narrow end and a wide end, said dissipating portion comprising an elongate resistive strip interconnected to said conductive strip along an edge at said wide end, said elongate resistive strip of a second constant thickness and comprising second arcuate side edges mutually converging between said wide end and a tip;
wherein each of said second arcuate side edges is a differentiable continuation of a respective one of said first arcuate side edges and each of said elongate conductive strips is interconnected at said narrow end to a respective one of the pair of conductors.

2. The antenna of claim 1, wherein each of said like elements further comprises an elongate feed positioned lengthwise between said narrow end and said respective one of the pair of conductors, said feed comprising a conductive strip of said constant thickness and having a constant width substantially the same as said narrow end.

3. The antenna of claim 1, wherein the transmission line is unbalanced and wherein one of said elements further comprises a balun between said narrow end and the respective one of the pair of conductors.

4. The antenna of claim 1, wherein each of said pair of first arcuate side edges has a taper profile selected from the group consisting of elliptical and exponential.

5. The antenna of claim 1, wherein the micro strip antenna is coplanar and each of said elements are on the same surface of said planar substrate.

6. The antenna of claim 1, wherein the micro strip antenna is antipoidal and each of said elements are on opposite surfaces of said planar substrate.

7. The antenna of claim 1, wherein said planar substrate is a printed circuit board and said first element and said second element are formed by depositing a conductive layer on said planar substrate.

8. A scanning element for use in a microwave scanning system, comprising:
a pair of like substantially flat wideband antennas, each of said antennas comprising a planar substrate fabricated from a dielectric material, a pair of radiating elements arranged on a surface of said substrate and a balun, each of said elements comprising a dissipating portion on said planar substrate portion, said dissipating portion comprising an elongate resistive strip interconnected to said conductive strip along an edge at said wide end, said elongate resistive strip of a second constant thickness and comprising second arcuate side edges mutually converging between said wide end and a tip;
wherein a first of said wideband antennas is positioned at right angles to a second of said wideband antennas.

9. The scanning element of claim 8, having a bandwidth between 1 GHz and 11 Ghz.

10. The scanning element of claim 8, wherein said radiating elements are arranged in a bowtie configuration.

* * * * *